(12) United States Patent
Sarmiento

(10) Patent No.: US 6,960,198 B2
(45) Date of Patent: Nov. 1, 2005

(54) TUBE AND SYRINGE HOLDING DEVICE FOR BLOOD COLLECTION AND FOR PRODUCING VACUUM INTO THE TUBE

(76) Inventor: Mario Sangiovanni Sarmiento, CP 11400, Montevideo (UY)

( * ) Notice: Subject to any disclaimer, the term of this patent is extended or adjusted under 35 U.S.C. 154(b) by 409 days.

(21) Appl. No.: 10/146,673

(22) Filed: May 15, 2002

(65) Prior Publication Data

US 2002/0173733 A1 Nov. 21, 2002

(30) Foreign Application Priority Data

May 16, 2001 (UY) .................................................. 26.711

(51) Int. Cl.⁷ ............................ A61B 19/00; A61B 5/00; A61M 5/32; B65D 81/00
(52) U.S. Cl. ....................... 604/411; 604/403; 600/576; 600/578
(58) Field of Search ....................... 604/4.01, 6.15–6.16, 604/18, 19, 27, 28, 30, 35–36, 38, 43–44, 500, 181–182, 187–189, 194–196, 200–201, 218, 110, 192, 198, 231–232, 234, 240–243, 246, 263–264, 271–272, 276, 523, 533–535

(56) References Cited

U.S. PATENT DOCUMENTS

| | | | | |
|---|---|---|---|---|
| 4,941,883 A | * | 7/1990 | Venturini | 604/186 |
| 4,943,283 A | * | 7/1990 | Hogan | 604/198 |
| 5,000,167 A | * | 3/1991 | Sunderland | 600/576 |
| 5,122,129 A | * | 6/1992 | Olson et al. | 604/240 |
| 6,500,129 B1 | * | 12/2002 | Mahurkar | 600/576 |
| 6,511,461 B2 | * | 1/2003 | Jonsson | 604/240 |

* cited by examiner

Primary Examiner—Patricia Bianco
(74) Attorney, Agent, or Firm—Pendorf & Cutliff

(57) ABSTRACT

The invention consists of a tube syringe holding device for blood collection and for producing vacuum into the tube which target is to enable the collection of blood, that can be manufactured in a light material where two bodies, one of them cylindrical and the other semi-cylindrical, both hollow and of the same length, form one structure. Its bottom ends are opened. The top end of the cylindrical body is continued by a conduit with a male luer adapter, and the top end of the semi-cylindrical one is continued by two conduits with threads.

14 Claims, 7 Drawing Sheets

DRAWING 1
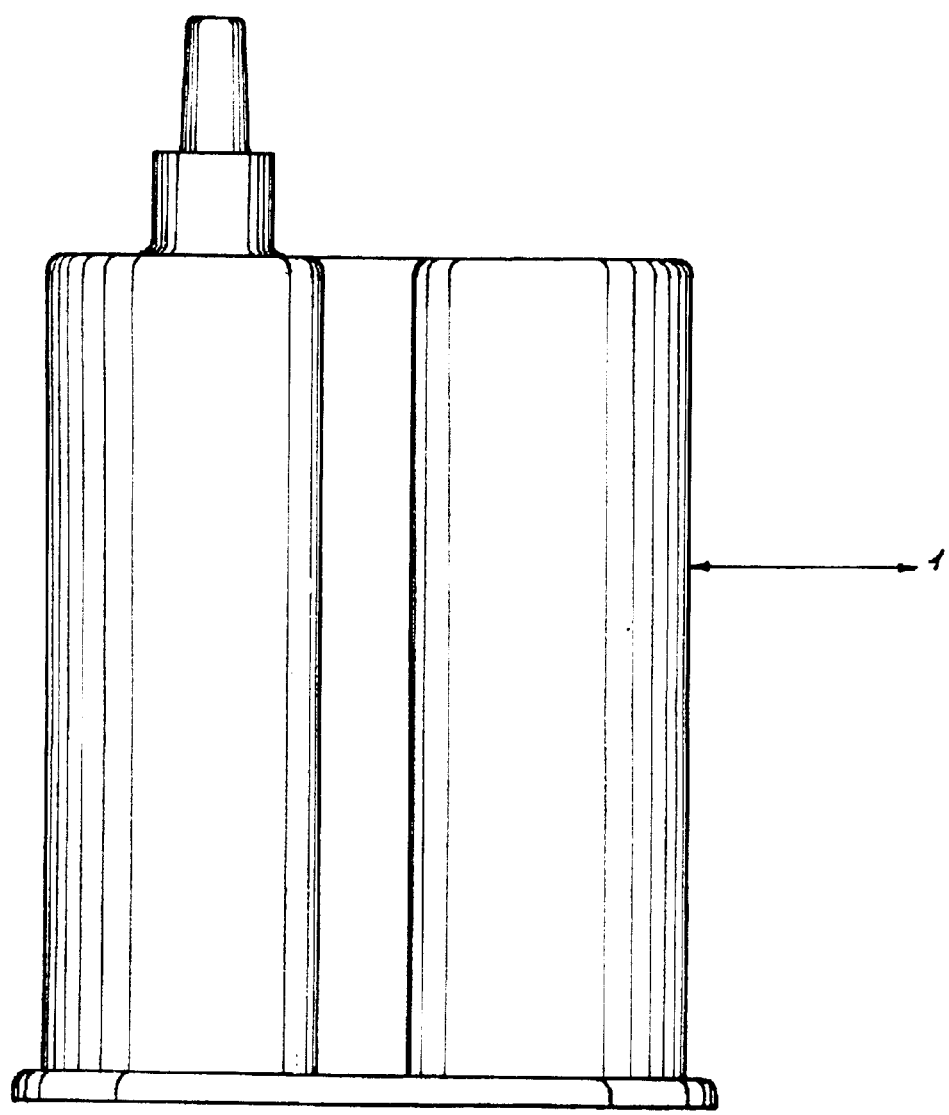

DRAWING 2
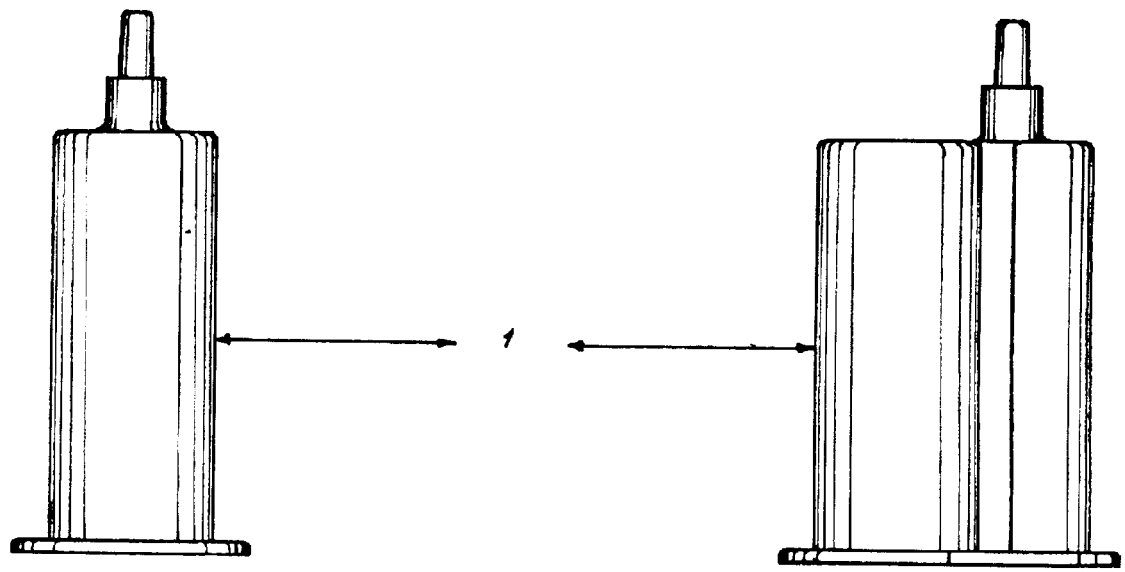
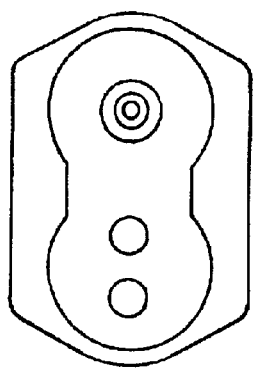 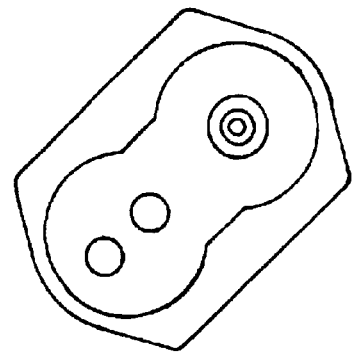

DRAWING 3
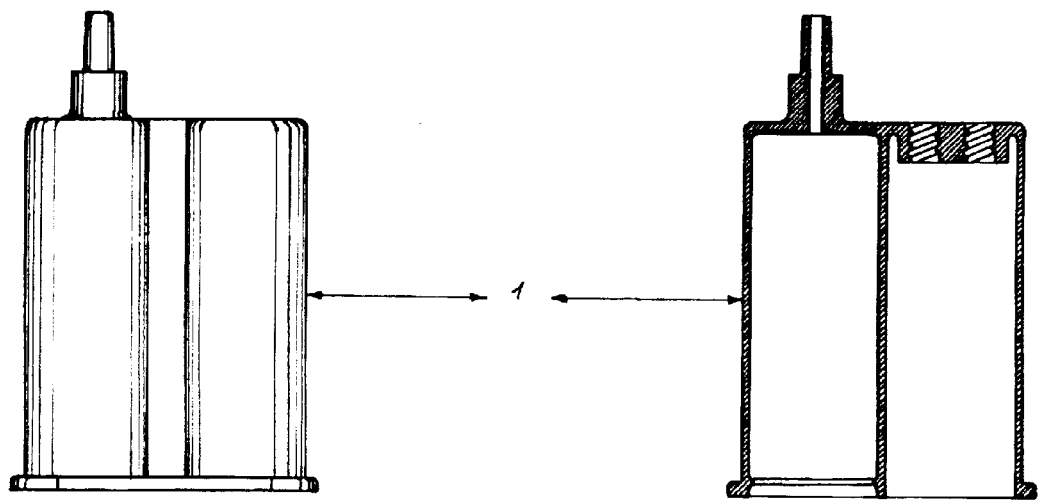
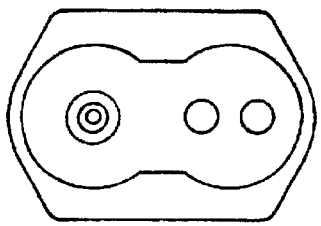   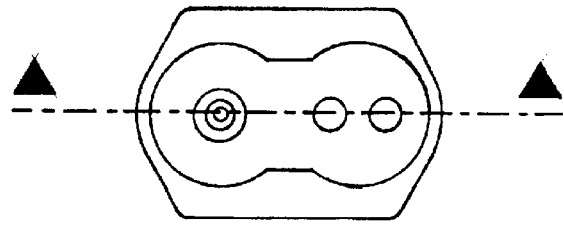

DRAWING 4
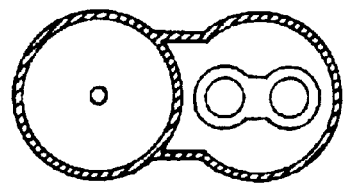
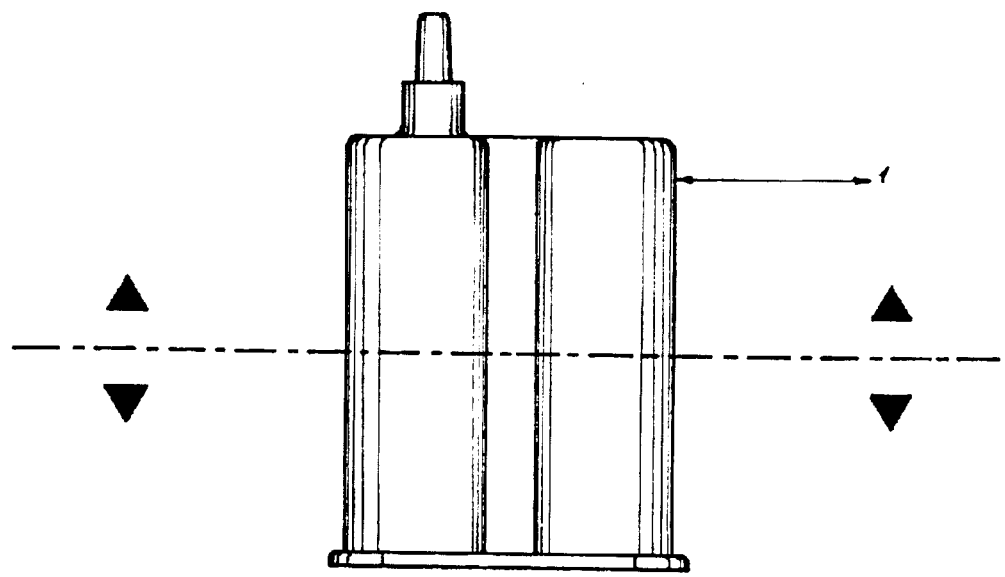
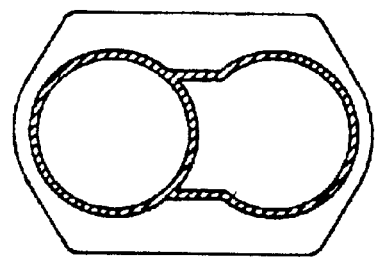

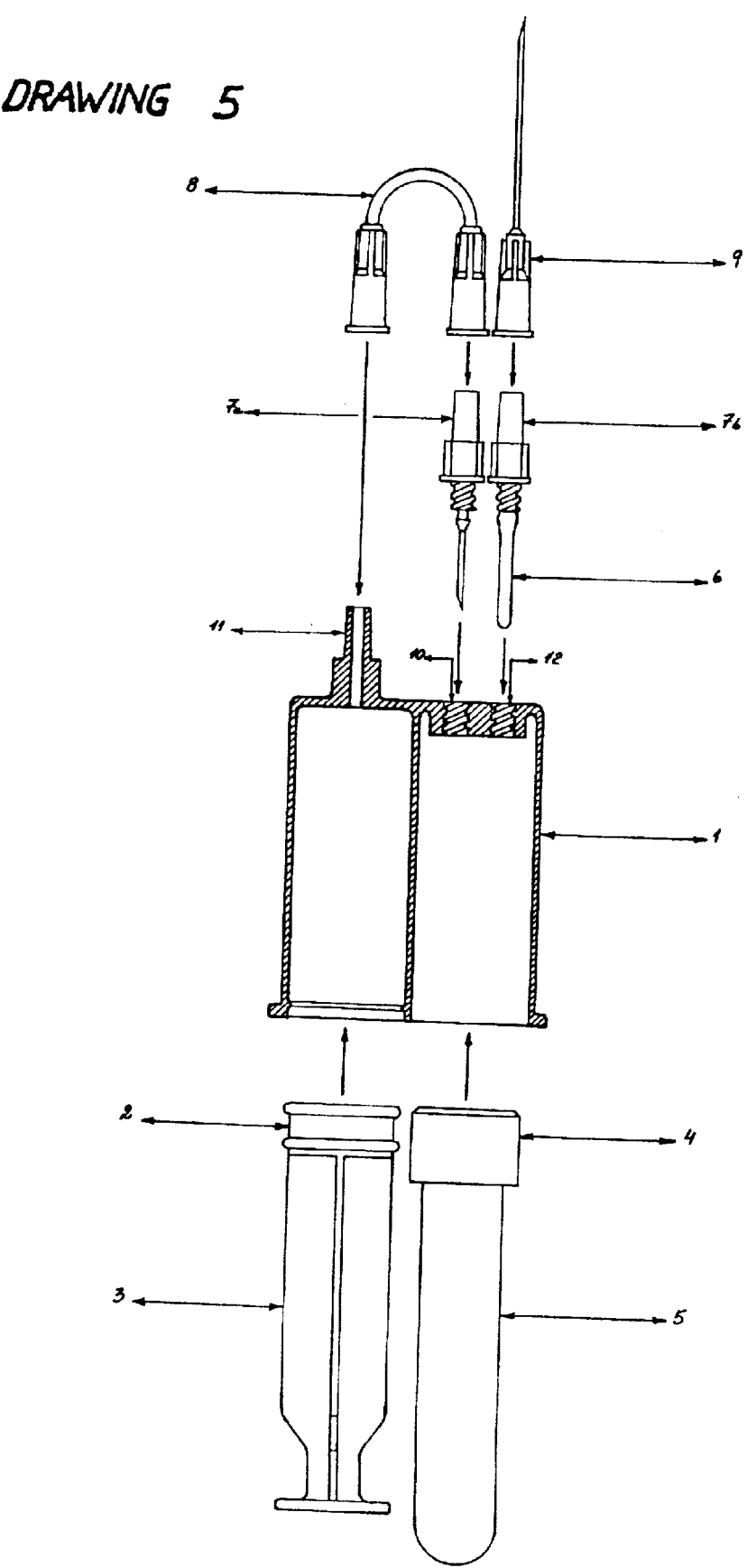

DRAWING 6
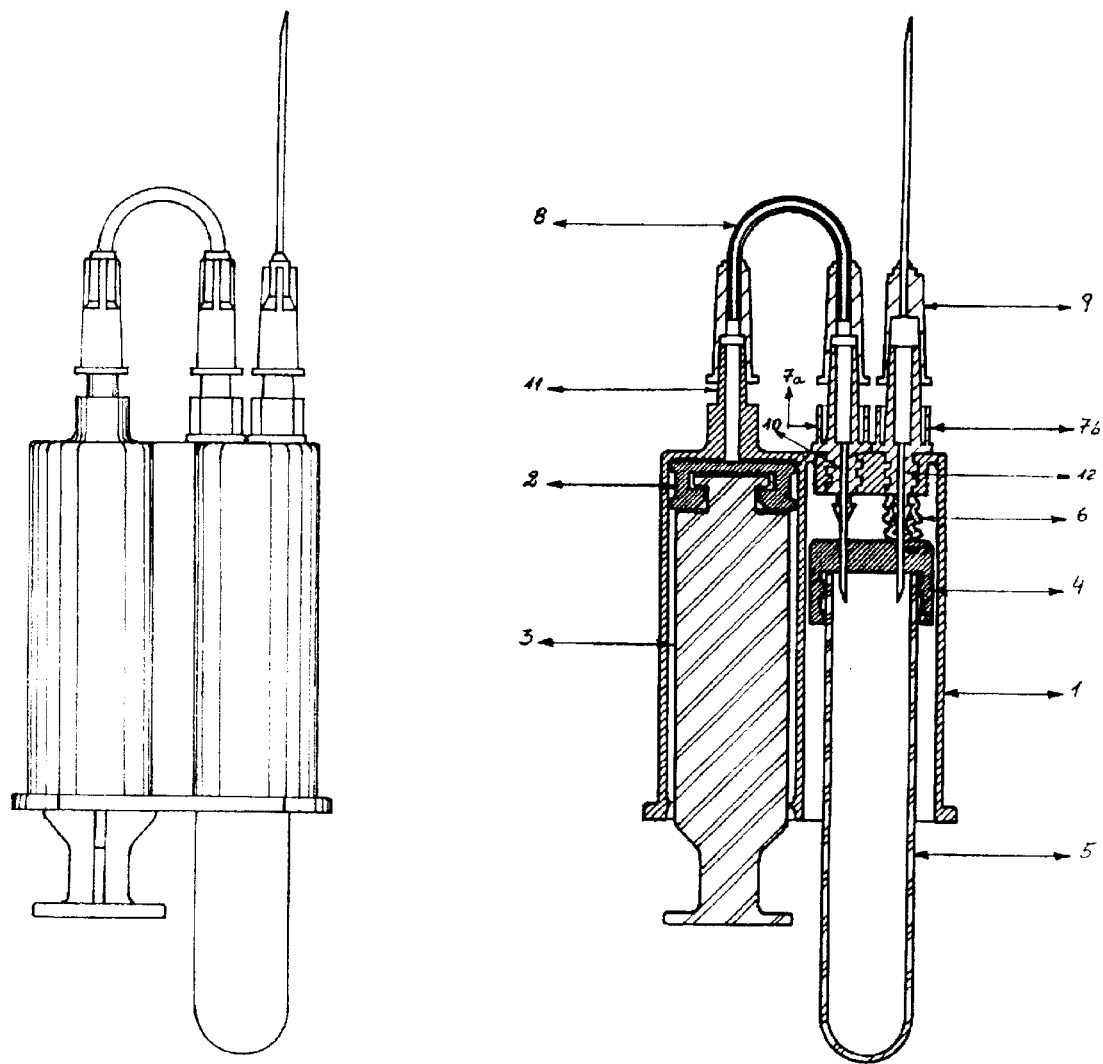

DRAWING 7
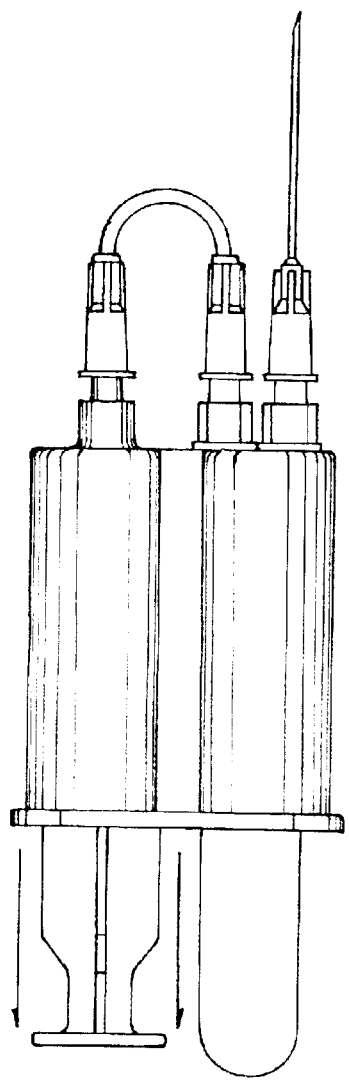

TUBE AND SYRINGE HOLDING DEVICE FOR BLOOD COLLECTION AND FOR PRODUCING VACUUM INTO THE TUBE

BACKGROUND OF THE INVENTION

1. Field of the Invention

The present invention concerns a holding device for blood collection devices.

2. Description of the Related Art

The already known blood collection devices are either syringes or those that demand the use of tubes with a vacuum treatment.

The blood colletion devices that demand the use of tubes with a vacuum treatment reveal two problems that the invention disclosed by this application solves through the substitution of tubes with a vacuum treatment by tubes without a vacuum treatment.

The first problem that the tubes with a vacuum treatment reveal is that they do not allow the person who manipulates the devices to correctly control the collection pressure of the blood that is carried by the vein because said collection pressure depends on the tube volume. Said unproper control carries as a consequence other problems. These problems are the following: a) It increases the hemolisis risk and, as a consequence, it reduces the quality of the blood samples; b) It makes difficult the obtainment of blood samples whenever the veins are very thin (e.g.: patients suffering from vein difficulties and children), increasing thrombosis or vein collapse risks.

The second problem that the tubes with a vacuum treatment reveal is that it is easy to loose the vacuum while manipulating the devices preventing the blood from being drawn into the tube.

Those problems appear while using, as for instance, devices disclosed by patents U.S. Pat. No. 6,024,710, EP 867.378 A2, and JP 1.291.830 A2.

On the other hand, the use of syringes for the collection of blood samples has two other characteristics that carry some problems that the invention that is claimed solves.

Firstly, the use of the syringes does not reach the higher level of the necessary asepsis for the correct manipulation of the blood samples. Said devices are opened so the blood can leak during their manipulation.

Secondly, while using the syringes, the blood is drawn into the tube only once it has been collected by using the syringes. That is to say, there are two consecutive actions, and this fact turns the quality of the blood sample risky.

The Applicant does not know of any other device comprising tubes without a vacuum treatment, enabling exactly the same manipulation quality offered as those devices comprising tubes with a vacuum treatment and that, in addition, solves the problems that said devices reveal and fulfills the asepsis and blood sample quality levels as the one disclosed in this application does, and has been disclosed before the priority date that is declared in this application.

SUMMARY OF THE INVENTION

The invention that is disclosed comprises a tube and syringe holding device for blood collection and for producing vacuum into the tube. The invention can be manufactured in a light material (e.g. a plastic material). Two bodies, both hollow, compose one structure.

One of these bodies is cylindrical, and the other is semi-cylindrical. The diameter and the length of the cylindrical one are similar to those of a holder having a completely opened bottom end and a top end that is continued by conduit of little diameter with a male luer adapter. The other body is semi-cylindrical because its walls are opened and partially lengthened to compose one structure together with the cylindrical body. The diameter of the semi-cylindrical body has to be proper so as to make possible the introduction and adjustment of the blood sample tubes of several diameters, one at a time. The semi-cylindrical body has the same length as the cylindrical one. The bottom end of the semi-cylindrical body is completely opened, and its top end is continued by two conduits with threads.

BRIEF DESCRIPTION OF THE DRAWINGS

In Drawing 1, a frontal view of the tube syringe holding device for blood collection and for producing vacuum into the tube can be appreciated (Number 1).

In Drawing 2, a lateral view and a 45° view of the tube syringe holding device for blood collection and for producing vacuum into the tube can be appreciated (Number 1), and also two views from above corresponding to the lateral view and the 45° view respectively.

In Drawing 3, a frontal view, and a frontal view with a frontal cut of the tube syringe holding device for blood collection and for producing vacuum into the tube (Number 1), and also two views from above corresponding to each of previously said views.

In Drawing 4 is a transversal cut, a view from below of the top side, a view from above of the bottom side of the tube syringe holding device for blood collection and for producing vacuum into the tube (Number 1).

In Drawing 5, it shows an explored view of the device according to the present invention.

In Drawing 6, it shows the present invention having the embolus couple with the plunger.

In Drawing 7, it shows a detailed description of the present invention during the working operation.

DETAIL DESCRIPTION OF THE INVENTION

One way of using the invention is with the following known elements: a) A plunger made of plastic material (Drawing 5, Number 3); b) An embolus made of, for instance, rubber or silicon (Drawing 5, Number 2); c) A rubber or silicon tube with female luer adapters in both its ends (Drawing 5, Number 8); d) Two needles with male luer adapters and threads (Drawing 5, Number 7a and 7b); e) A rubber cover (Drawing 5, Number 6); f) A needle with female luer adapter (Drawing 5, Number 9; and g) Tubes without a vacuum treatment (Drawing 5, Number 5) of several diameters with rubber seals (Drawing 5, Number 4).

The embolus (Drawing 6, Number 2) is coupled together with the plunger (Drawing 6, Number 3). Once coupled together, they are introduced into the cylindrical body of the device (Drawing 6, Number 1). One of the needles with male luer adapter and threads (Drawing 6, Number 7a) is threaded in one of the conduits on the top end of the semi-cylindrical body (Drawing 6, Number 10). The rubber tube with the female luer adapter in its ends (Drawing 6, Number 8) is coupled together with the male luer adapter of the cylindrical body (Drawing 6, Number 11) and with said needle with ale luer adapter and thread (Drawing 6, Number 7a). The other needle with male luer adapter and thread (Drawing 6, Number 7b) has a rubber cover (Drawing 6, Number 6), and is threaded to the second conduit of the semi-cylindrical body (Drawing 6, Number 12). The needle with female luer adapter (Drawing 6, Number 9) is coupled together with one of the needles with male luer adapter (Drawing 6, Number 7b). The tube without a vacuum treatment (Drawing 6, Number 5) with rubber seal (Drawing 6, Number 4) is introduced into the semi-cylindrical body. The needles perforate the rubber seal (Drawing 6, Numbers 7a and 7b).

In relation to the way of manipulating the tube syringe holding device for blood collection and for producing vacuum into the tube, once the patient has been picked with the needle that enables the blood to be collected (Drawing 7 Number 9), the manipulation of the plunger and the embolus that have been coupled together with the cylindrical body (Drawing 7, Numbers 3 and 2) enable the blood to be drawn by aspiration through one of the needles threaded to the cylindrical body (Drawing 7, Number 7b) to the tube without a vacuum treatment that is also coupled together with the cylindrical body (Drawing 7, Numbers 5 and 13) by way of removing the air from inside the tube. Said air is simultaneously aspired through the second needle threaded to the semi-cylindrical body (Drawing 7, Number 7a) to be sent to the cylindrical body. In effect, the embolus is moved inside the cylindrical body, and this way, the air from the tube is sent to said cylindrical body enabling the blood to be drawn into the tube simultaneously.

The use of the tube syringe holding device for blood collection and for producing vacuum into the tube allows to produce vacuum into the tube in a controlled way because it enables to control the movement speed of the embolus coupled together with the cylindrical body of the device's structure.

The invention is different from the syringes for blood collection because said syringes for blood collection are independent elements. In effect, only after the blood has been collected, the blood sample can be drawn into the tube. The manipulation carries: a) Hemolisis risk; b) Contamination risk, both in relation to the person who manipulates the sample as in relation to the blood sample.

The invention is different from the tubes with a vacuum treatment system because said system: a) Needs tubes with a vacuum treatment; b) Does not enable the proper control of the aspiration pressure; c) Can carry the hemolisis risk; d) It is not advisable in case of patients with vein difficulties or children.

On the contrary, the tube syringe holding device for blood collection and for producing vacuum into the tube is better than the tubes with a vacuum treatment system because: a) It enables a proper control of the blood aspiration pressure due to the fact that the vacuum can be produced in a controlled way allowing to avoid the hemolisis risk; b) As a consequence of what has just been said, it enables its use in all kind of patients, being irrelevant their good or bad health, their physical condition or their age, so that it reveals to be particularly useful in case of patients suffering from vein difficulties and children avoiding thrombose or vein collapse risks.

On the other hand, the tube syringe holding device for blood collection and for producing vacuum into the tube is better than the syringe for blood collection because: a) It allows a better asepsis and a lower biological risk due to the fact that it enables the manipulation of the blood sample with a tube system completely shut; b) It enables an efficacious and easy manipulation of the blood samples, because the blood is drawn through the needle of blood admission, being drawn simultaneously into the tube or tubes that can be exchanged increasing the samples quality.

In addition, the tube syringe holding device for blood collection and for producing vacuum into the tube that is disclosed can be either reuseable or disposable while syringes are always disposable. In effect, after using the tube syringe holding device for blood collection and for producing vacuum into the tube, only the needles for blood collection and the coupled needle that guides the blood into the tube have to be thrown away after being unthreaded from the holding device.

In relation to the way of industrially manufacturing the invention, it can be manufactured using moulds for plastic material.

What is claimed is:

1. A tube syringe holding device for blood collection, the holding device comprising:
    a cylindrical body having a bottom end, a top end, a diameter and a length; and
    a semi-cylindrical body having a bottom end, a top end, a diameter and a length;
    wherein the cylindrical body and semi-cylindrical body form one structure; and
    wherein the cylindrical body and semi-cylindrical body are adapted to produce a vacuum into the tube;
    wherein the cylindrical body further comprises a male luer adapter at the top end;
    wherein the semi-cylindrical body comprises a first threaded female luer adapter and a second male luer adapter at the top end.

2. A tube syringe holding device, according to claim 1, further comprising an elongated tube having a first and second female luer adapter at each end, wherein the first female luer of the elongated tube is connected to the male luer adapter of the cylindrical body.

3. A tube syringe holding device, according to claim 2, further comprising a first and second needle having a threaded male luer adapter, wherein each needle is connected to the threaded female luer adapter of the semi-cylindrical body.

4. A tube syringe holding device, according to claim 3, wherein the second female luer of the elongated tube is connected to the first needle having a threaded male luer adapter.

5. A tube syringe holding device, according to claim 4, wherein a needle having a female luer adapter is connected to the second needle having a threaded male luer adapter.

6. A tube syringe holding device, according to claim 5, further comprising a plunger adapted to be introduced into the bottom end of the cylindrical body and a blood sample tube adapted to be introduced into the bottom end of the semi-cylindrical body; wherein the blood sample tube contains air.

7. A tube syringe holding device, according to claim 6, wherein the semi-cylindrical body is adapted to receive blood samples tubes having different diameters.

8. A tube syringe holding device, according to claim 7, wherein the blood is drawn into the tube while it is being collected from the patient.

9. A tube syringe holding device, according to claim 6, wherein the holding device produces a vacuum by aspirating air from blood test tubes at the same time the blood is drawn.

10. A tube syringe holding device, according to claim 1, wherein the diameter and length of the cylindrical body are similar to those of the holding device.

11. A tube syringe holding device, according to claim 1, wherein the semi-cylindrical body further includes two walls that are opened and partially lengthened to form one structure with the cylindrical body.

12. A tube syringe holding device, according to claim 1, wherein the length of the semi-cylindrical body is similar to the length of the cylindrical body.

13. A tube syringe holding device, according to claim 1, wherein the holding device is reusable or disposable.

14. A tube syringe holding device for blood collection, the holding device comprising:
- a cylindrical body having a bottom end, a top end, a diameter and a length; and
- a semi-cylindrical body having a bottom end, a top end, a diameter and a length;
- wherein the cylindrical body and semi-cylindrical body form one structure; and
- wherein the cylindrical body and semi-cylindrical body are adapted to produce a vacuum into the tube;
- wherein the cylindrical body further comprises a male luer adapter at the top end;
- wherein the semi-cylindrical body further comprises at the top end two threaded conduits.

* * * * *